(12) United States Patent
Szuchmacher

(10) Patent No.: US 11,969,301 B2
(45) Date of Patent: Apr. 30, 2024

(54) SMART FLEXIBLE LIGHTING SYSTEM FOR OPERATING ROOMS

(71) Applicant: Mauricio Szuchmacher, Lake Grove, NY (US)

(72) Inventor: Mauricio Szuchmacher, Lake Grove, NY (US)

( * ) Notice: Subject to any disclaimer, the term of this patent is extended or adjusted under 35 U.S.C. 154(b) by 269 days.

(21) Appl. No.: 17/723,137

(22) Filed: Apr. 18, 2022

(65) Prior Publication Data

US 2023/0329827 A1    Oct. 19, 2023

(51) Int. Cl.

| | | |
|---|---|---|
| *A61B 90/35* | (2016.01) | |
| *A61B 90/00* | (2016.01) | |
| *A61C 1/08* | (2006.01) | |
| *A61D 99/00* | (2006.01) | |
| *F21V 21/15* | (2006.01) | |
| *F21V 21/32* | (2006.01) | |
| *G06T 1/20* | (2006.01) | |
| *G10L 15/18* | (2013.01) | |
| *G10L 15/22* | (2006.01) | |

(Continued)

(52) U.S. Cl.
CPC ............ *A61B 90/35* (2016.02); *A61B 90/361* (2016.02); *A61C 1/088* (2013.01); *A61D 99/00* (2013.01); *F21V 21/15* (2013.01); *F21V 21/32* (2013.01); *G06T 1/20* (2013.01); *G10L 15/18* (2013.01); *G10L 15/22* (2013.01); *G16H 40/20* (2018.01); *F21W 2131/20* (2013.01); *G10L 2015/223* (2013.01)

(58) Field of Classification Search
CPC ...... F21S 2/005; G06T 1/20; G10L 2015/223; G10L 15/18; G10L 15/22; G10L 15/26; G16H 40/20
See application file for complete search history.

(56) References Cited

U.S. PATENT DOCUMENTS

| | | |
|---|---|---|
| 4,597,030 A | 6/1986 | Brody |
| 5,353,786 A | 10/1994 | Wilk |

(Continued)

FOREIGN PATENT DOCUMENTS

| | | | |
|---|---|---|---|
| CA | 2465524 C | 9/2007 | |
| WO | WO-2012095323 A1 * | 7/2012 | ......... A61B 19/5202 |

(Continued)

*Primary Examiner* — Zheng Song

(57) ABSTRACT

A smart flexible operating room lighting system with a control system utilizing artificial intelligence (AI) modules may be coupled to a wall, ceiling, or fixture of and mobile in a facility. The lighting system can modularly accommodate multiple illumination arms and incorporate microphones thereon, permitting the vocal control using the control system for hands free operations. The control system controls the movements of the illumination arms to desired positions and orientations via motor-driven actuators and position sensors thereon. The lighting system may include a speaker and a camera to facilitate two-way communications with a user via the control system to facilitate demonstrations for individuals undergoing tutelage in the facility. Further, a cover with a transparent front end may be provided to be slipped over the lighting system and securing through a cover fastener. Thus, the present invention provides reliable sanitary measures while facilitating efficient operations via the smart flexible illumination arms.

20 Claims, 11 Drawing Sheets

(51) Int. Cl.
  *G16H 40/20* (2018.01)
  *F21W 131/20* (2006.01)

(56) References Cited

U.S. PATENT DOCUMENTS

| | | | |
|---|---|---|---|
| 6,874,908 B2 | 4/2005 | Sharrah | |
| D586,528 S | 2/2009 | Lowry | |
| D632,413 S | 2/2011 | Teufel | |
| 9,587,792 B1 | 3/2017 | Parsons | |
| 9,937,936 B2 | 4/2018 | Brooks | |
| 11,191,607 B2 | 12/2021 | Szuchmacher | |
| 2001/0025905 A1* | 10/2001 | Carpenter | A61B 90/50 248/231.71 |
| 2004/0090776 A1 | 5/2004 | Yang | |
| 2005/0099824 A1* | 5/2005 | Dowling | A61B 90/36 362/572 |
| 2006/0012980 A1* | 1/2006 | Mize | F21V 21/32 362/198 |
| 2006/0256561 A1* | 11/2006 | Smith | F21V 17/007 362/267 |
| 2009/0303739 A1* | 12/2009 | Garcia | B60Q 3/88 362/220 |
| 2010/0030033 A1 | 2/2010 | Farley | |
| 2013/0201688 A1* | 8/2013 | Glass | F21V 14/06 362/285 |
| 2014/0221754 A1 | 8/2014 | Cabaud | |
| 2017/0030573 A1* | 2/2017 | Alexanderson | H05B 47/115 |
| 2019/0199915 A1 | 6/2019 | Coiseur | |
| 2023/0248466 A1* | 8/2023 | Petrucci | A61B 90/30 700/276 |

FOREIGN PATENT DOCUMENTS

| | | | | |
|---|---|---|---|---|
| WO | WO-2018144820 A1 * | 8/2018 | | A61B 17/00234 |
| WO | WO-2021226134 A1 * | 11/2021 | | A42B 3/042 |

* cited by examiner

SMART FLEXIBLE LIGHTING SYSTEM FOR OPERATING ROOMS

The present invention relates generally to lighting systems. More specifically, the present invention relates to a modular lighting system that is particularly employed for intraoperative settings.

BACKGROUND OF THE INVENTION

Optimal quality lighting is critical for any medical facility, no matter if it is an ER (emergency room), an OR (operating room), a trauma bay, a surgical office, or an exam room in a doctor's office. This applies to dentist offices as well, for dental implants, and veterinary surgery rooms for large or small animals. All medical, dental, and veterinary professionals need excellent lighting when providing care.

Presently, lighting is known to the art, as are lighting arrangements in an intraoperative/surgical setting where the lighting requires frequent manipulation and sterilization considerations. Conventional intraoperative lighting generally invokes a bulky lighting system that is tedious to manipulate once a procedure is underway. Most, if not all, existing surgical lights do have drawbacks.

For example, mounted surgical lights that are ceiling or wall-mounted do provide plenty of light, but they do lack significant flexibility. No matter how much light they produce, they are still fixed at their base. They may have quite a reach, but they cannot be moved into the next room thus lacking mobility. Additionally, it is very important to mount the light source exactly where it will be needed and at the correct height. Any redesign of the facility layout or furniture can cause the mounted light device to be unusable. Further, a light source should be arranged appropriately so that a patient lying in an exam chair or on an examination table is not staring directly into the bright light.

On the other hand, many existing portable surgical lights are likely to get in the way of the medical professionals as they perform the procedure. The light source would then need to be moved, or at least slightly adjusted any time the patient has a positional change, or the doctor needs to see from a different angle. Additionally, most portable surgical lights do not provide the flexibility to easily adjust the surgical lamp head for optimal viewing of the surgical site. Tracking a portable surgical light's location and making sure it is available for a procedure are common problems. There is always the possibility that a portable surgical light will be in another room when it is needed, or it is unavailable because it is already in use.

It is therefore the objective of the present invention to introduce a lighting system that in a first embodiment may be coupled to an extraneous ceiling, connected to a conventional power grid of the facility through a base. Whereupon the base a plurality of ports is disposed that may accommodate an equal number of illumination arms to be modularly coupled therein. Additionally, the illumination arm may be guided into a particular orientation and direction by a handle along the illumination arm. Further, the illumination arm may comprise an optional microphone thereon, permitting the vocal control of the illumination means as executed by a processor within the base. An illumination head located at the distal end of the illumination arm opposite the jack and base side may further accommodate thereon a speaker and a camera. Thus, the present invention may facilitate two-way communications by the speaker with an extraneous personal computing (PC) device, or even facilitate demonstrations for individuals undergoing tutelage in the particular facility's profession. Further, the present invention may employ a stand that further facilitates modularity of the apparatus by permitting motion along a plurality of wheels and controls localized to a stand casing atop a column and a plurality of legs/wheels. Further still, a cover may be provided to the at least one illumination arm. Wherein the illumination arm having a smaller volume than traditional intraoperative/surgical/medical lighting, permits the tubular cover to be slipped over the at least one illumination arm, and securing through a cover fastening means. Thus, the present invention provides reliable sanitary measures aligned to standard conventions, while further facilitating a smaller operable device through the illumination arms, and the direction of the illumination head may be manipulated through the handle. Additionally, by providing the illumination arm with a jack that compliments an individual port of the plurality of ports, the illumination arm may be modularly assigned, replaced, sanitized, and added as the situation demands in a capacity extensively more expedient than conventional overhead assemblies. Further, by providing the microphone alongside a processor, the present invention may facilitate hands free operations, furthering the sanitary measures of the present invention while simultaneously affording two-way communications and educational operations through the optional speaker and the optional camera.

SUMMARY OF THE INVENTION

A smart flexible operating room lighting system is designed to be coupled to an extraneous wall, ceiling, or fixture, and connected to a conventional power grid of a medical, dental, or veterinary facility. Through a solid base, the smart flexible lighting system can accommodate multiple illumination arms to be modularly coupled therein. By adapting the solid base to existing mounting mechanisms used to mount lights on ceilings, walls, and fixtures of intraoperative facilities, the smart flexible lighting system can be used to conveniently and efficiently replace existing conventionally lighting systems. Additionally, each illumination arm is flexible, thus can be guided into a particular orientation and direction. By providing the illumination arm with a jack that compliments an individual port of a plurality of ports on the base, the illumination arm may be modularly assigned, replaced, sanitized, and added as the situation demands in a capacity extensively more expedient than conventional overhead systems.

Each illumination arm may comprise one or more microphone thereon, permitting the vocal control of the illumination arm as executed by a processor of a control system of the smart flexible lighting system. By providing the microphone alongside the processor, the flexible lighting system may facilitate hands free operations, offering sanitary measures of the flexible lighting system. A speaker and a camera can be installed on the illumination arm to facilitate two-way communications via the processer with an extraneous personal computing (PC) device, or even facilitate demonstrations for individuals undergoing tutelage in the particular facility's profession. The illumination arm may comprise one or more microphone thereon, permitting the vocal control of the illumination arm as executed by a processor of the control system. Additionally, the illumination arm may include a plurality of position sensors that provides position and/or orientation of the illumination head as inputs to the processor of the control system. Further, the present invention may accommodate a speaker and a camera installed on the illumination arm to facilitate two-way communications with the extraneous user PC device, or even facilitate demonstrations for individuals undergoing tutelage in the particular facility's profession. The processor of the smart flexible lighting system uses multiple inputs from the plurality of position sensors, the camera, the microphone, to facilitate automatic control of the illumination arms and the communications between the present invention and the user's PC device via artificial intelligence (AI) modules. The AI modules of the present invention include, but are not limited to, natural language processing (NLP) module, deep learning module, computer vision module, and any other suitable module using an AI technology. The smart flexible lighting system may employ a stand that further facilitates modularity of the apparatus by permitting motion along a plurality of wheels and controls localized to a stand casing atop a column and a plurality of legs/wheels.

Further, a cover with a transparent front end may be provided to the at least one illumination arm of the flexible lighting system. Since the illumination arm has a smaller volume than traditional intraoperative, surgical, and/or medical lighting, the flexible lighting system permits the tubular cover to be slipped over the at least one illumination arm and securing through a cover fastener. Thus, the flexible lighting system provides reliable sanitary measures aligned to standard conventions, while further facilitating a smaller operable device through the illumination arms.

DETAIL DESCRIPTIONS OF THE INVENTION

Figure 1:
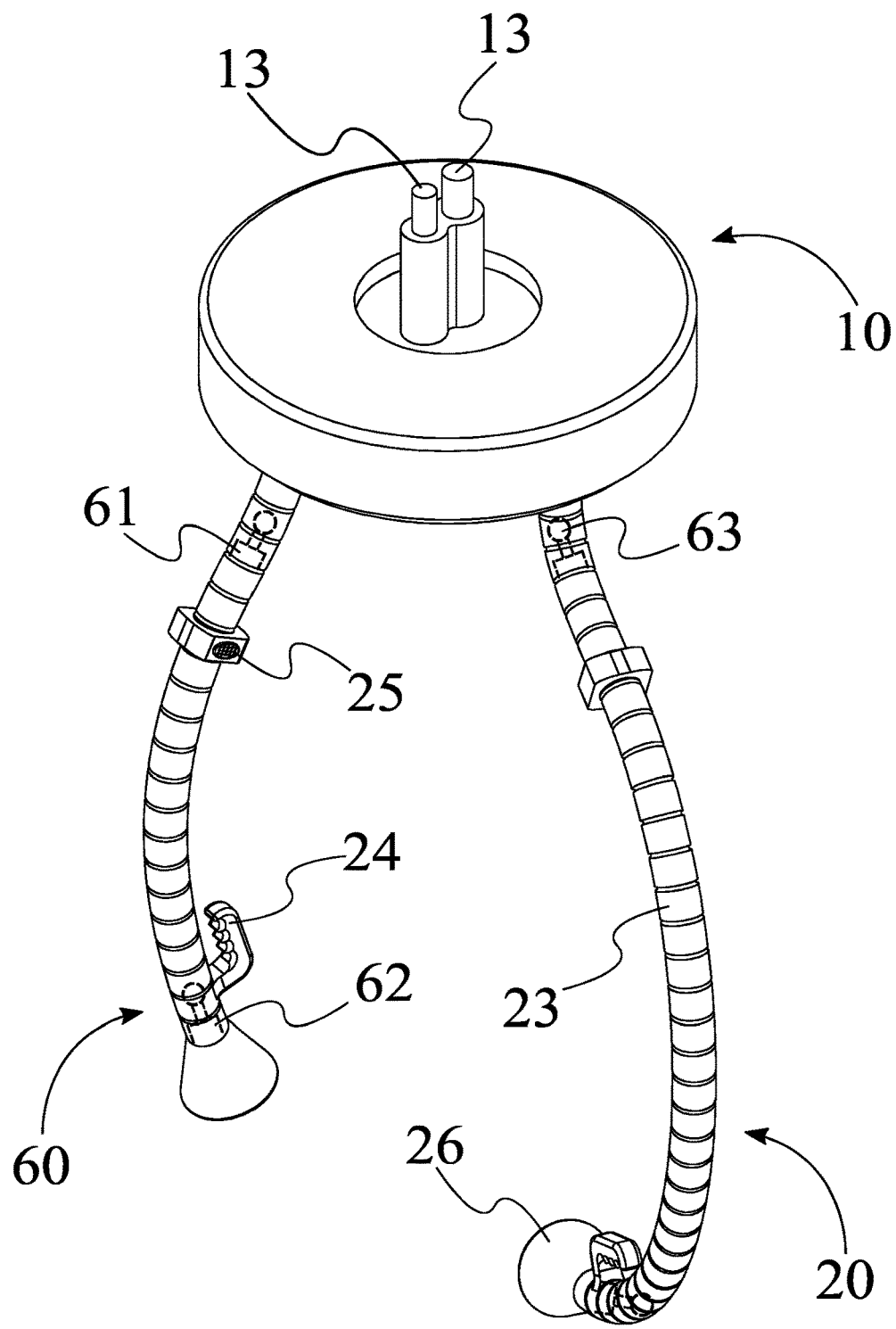
FIG. 1 is a perspective view of the preferred embodiment of a smart flexible lighting system of the present invention, where a base is observed with a plurality of cables protruding from the top surface thereof.
Figure 2:
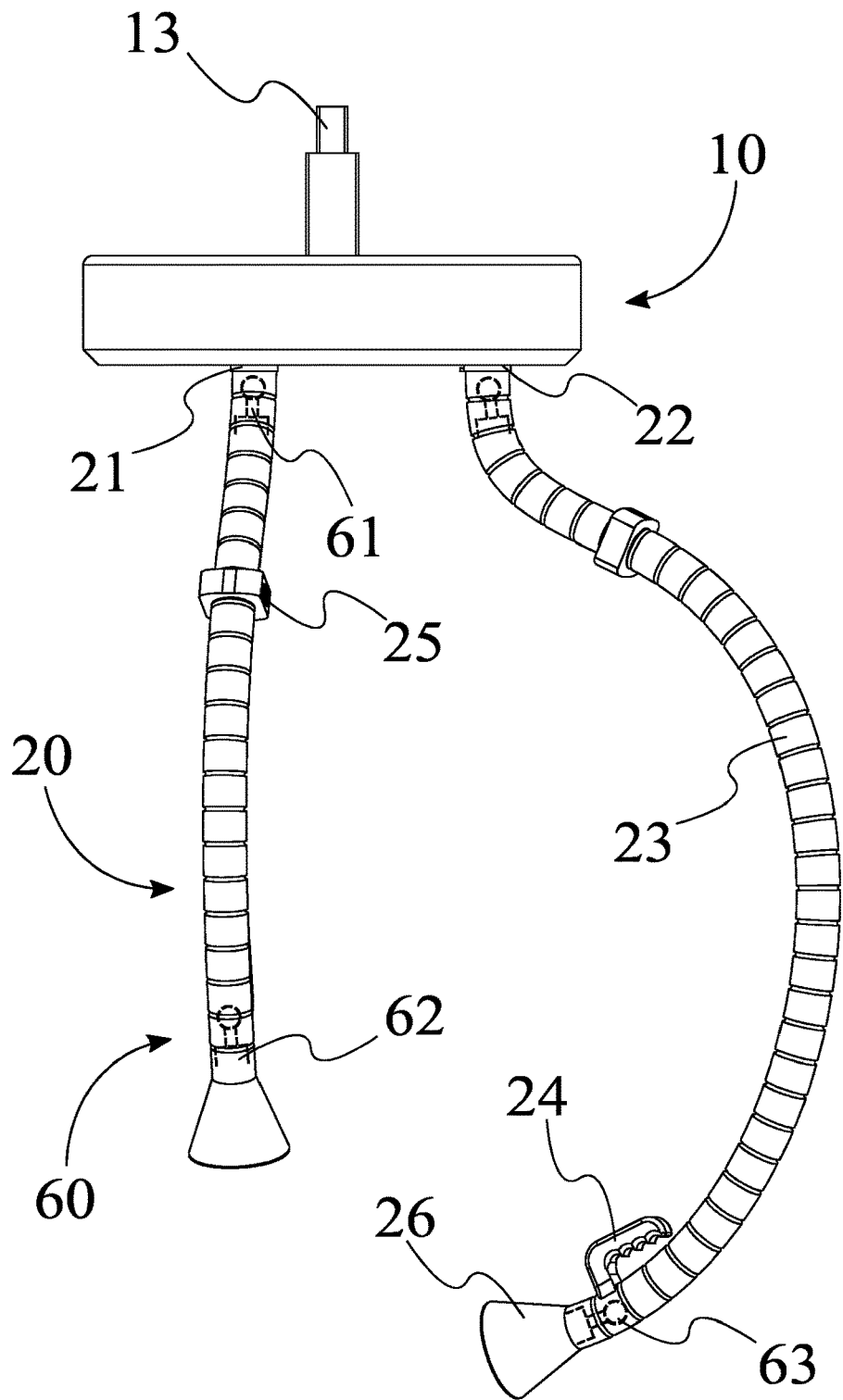
FIG. 2 is a front view of the present invention, wherein a jack base is observed flush with the underside of the base and at the distal end of each illumination arm.
Figure 3:
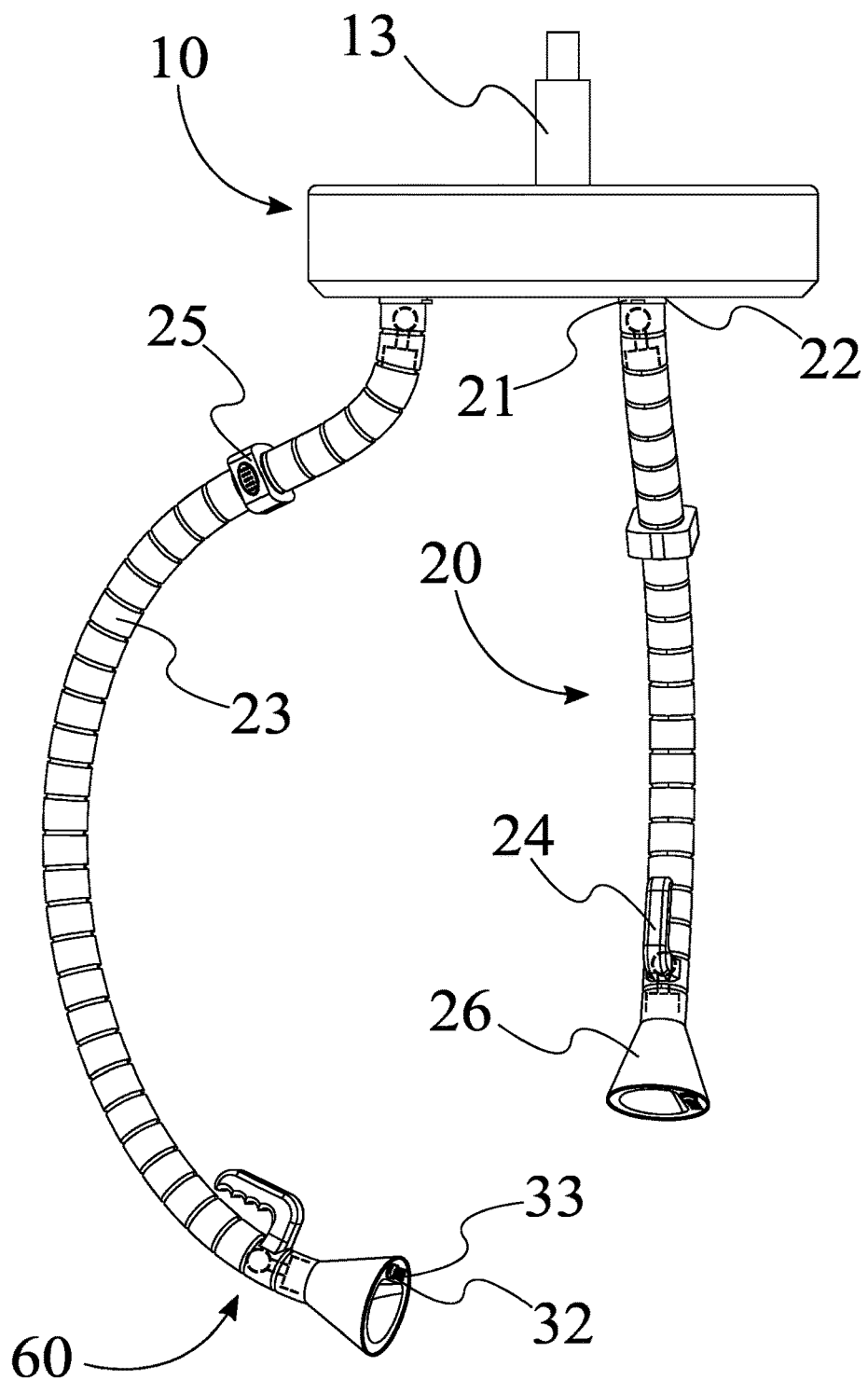
FIG. 3 is a rear view of the present invention, wherein a microphone is observed along the illumination arm between the jack base and a handle.
Figure 4:
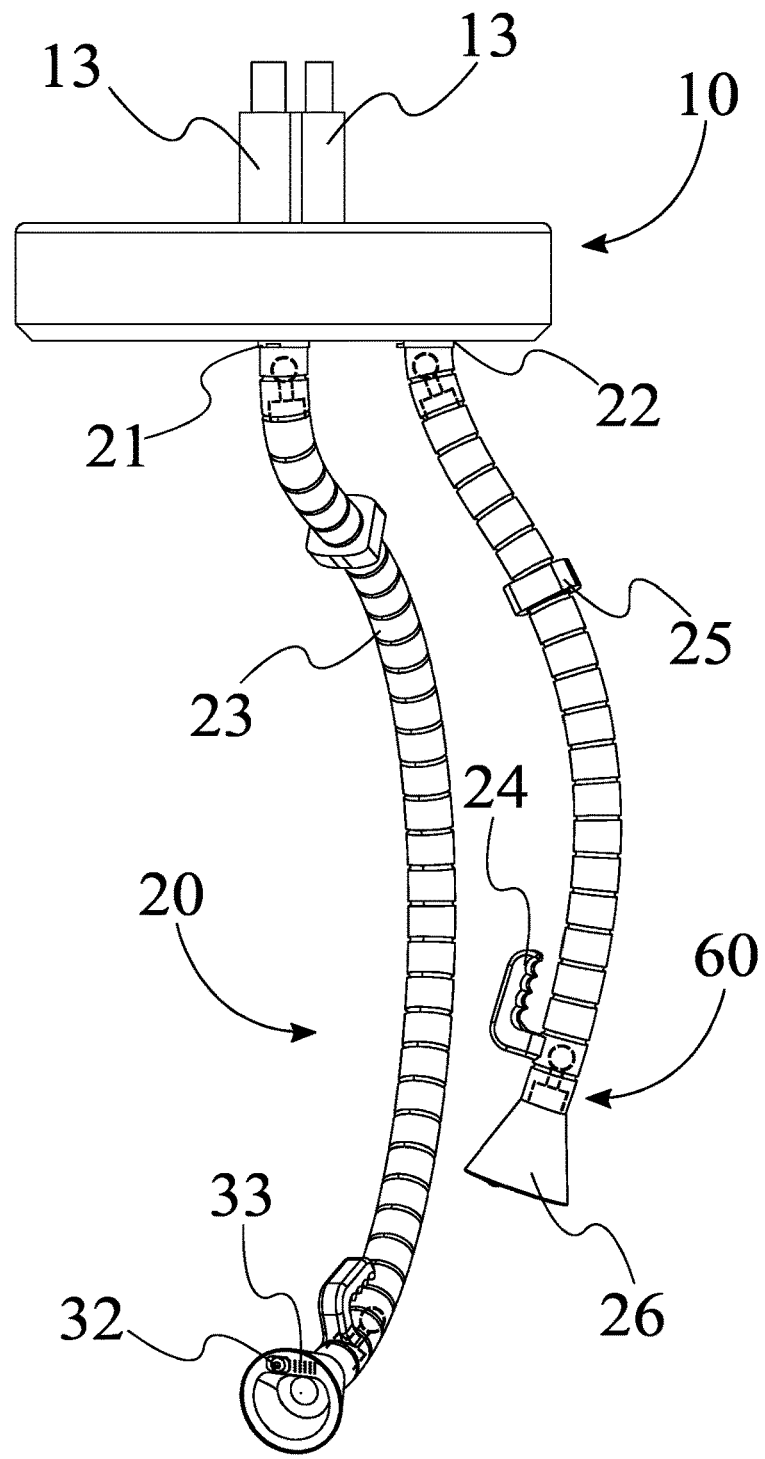
FIG. 4 is a right view of the present invention.
Figure 5:
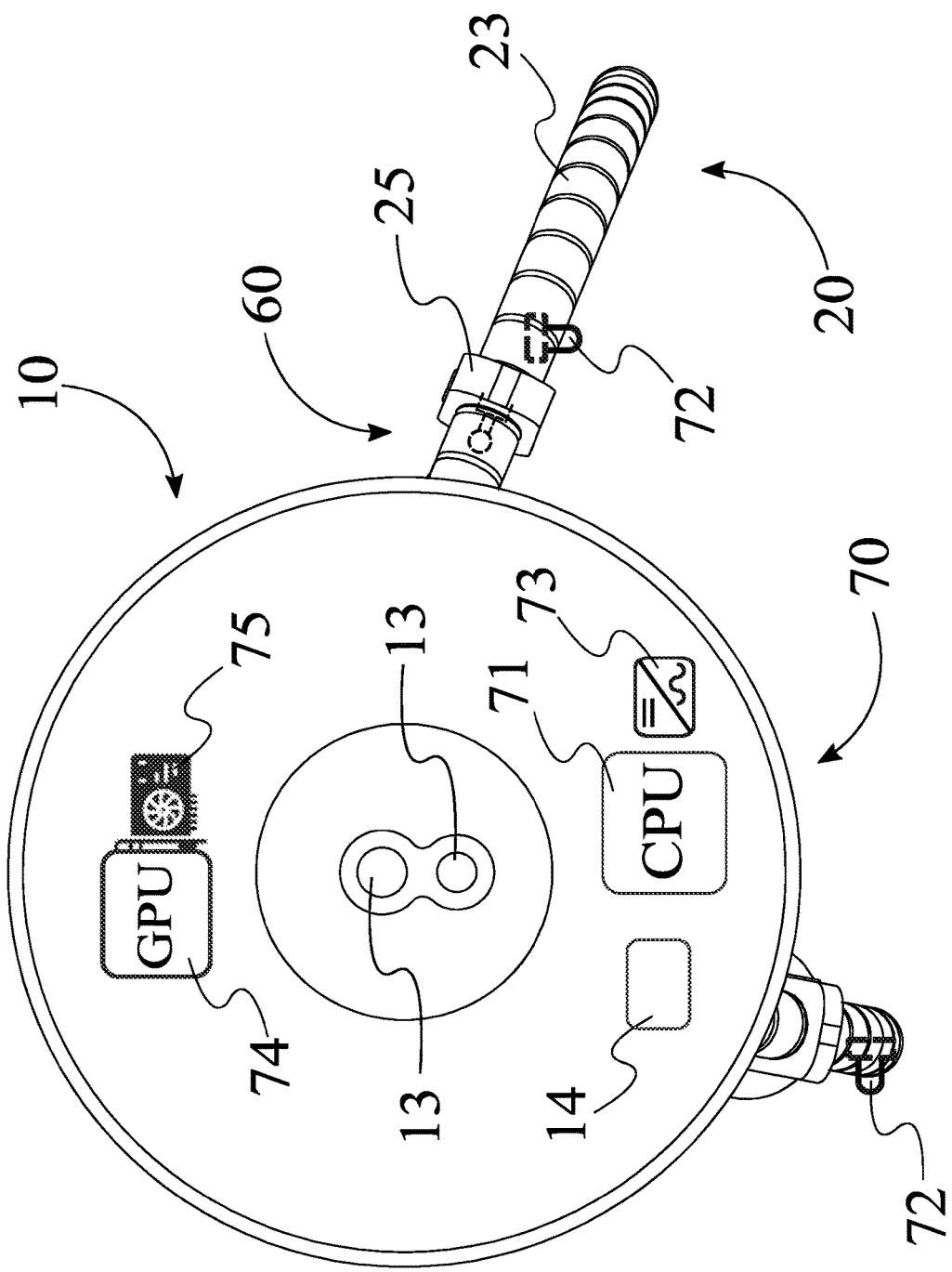
FIG. 5 is a top view of the present invention, wherein a control system comprises a processor, an analog/digital (A/D) converter, a graphical processing unit, and a cooling system.

All illustrations of the drawings are for the purpose of describing selected versions of the present invention and are not intended to limit the scope of the present invention.

As can be seen in FIG. 1 to FIG. 11, the present invention provides a smart operating room lighting system that may be coupled to an extraneous wall, ceiling, or fixture, and connected to a conventional power grid of the facility. The smart lighting system can accommodate multiple illumination arms to be modularly coupled therein. Additionally, each illumination arm of the present invention is flexible, thus can be guided into a particular orientation and direction by a handle along the illumination arm and/or a control system that uses multiple inputs and artificial intelligence (AI) modules. The illumination arm may comprise one or more microphone thereon, permitting the vocal control of the illumination arm as executed by a processor of the control system. Further, the present invention may accommodate a speaker and a camera installed on the illumination arm to facilitate two-way communications with an extraneous personal computing (PC) device, or even facilitate demonstrations for individuals undergoing tutelage in the particular facility's profession. The AI modules of the present invention include, but are not limited to, natural language processing (NLP) module, deep learning module, computer vision module, and any other suitable module using an AI technology. In some embodiments, the present invention may employ a stand that further facilitates modularity of the apparatus by permitting motion along a plurality of wheels and controls localized to a stand casing atop a column and a plurality of legs/wheels. Additionally, a cover with a transparent front end may be provided to the at least one illumination arm, wherein the illumination arm having a smaller volume than traditional intraoperative, surgical, and/or medical lighting, permits the tubular cover to be slipped over the at least one illumination arm, and securing through a cover fastener. Thus, the present invention provides reliable sanitary measures aligned to standard conventions, while further facilitating a smaller operable device through the illumination arms. By providing the illumination arm with a jack that compliments an individual port of a plurality of ports, the illumination arm may be modularly assigned, replaced, sanitized, and added as the situation demands in a capacity extensively more expedient than conventional overhead assemblies. Further, by providing the microphone alongside the processor of the control system, the present invention may facilitate hands free operations, furthering the sanitary measures of the present invention while simultaneously affording two-way communications and educational operations through the speaker and the camera.

As can be seen in FIG. 1 to FIG. 6, the present invention comprises a smart flexible lighting system for medical, dental, and veterinary facilities. More specifically, the flexible lighting system of the present invention comprises a base 10, at least one illumination arm 20, at least one actuator 80, and a control system 70. The base 10 comprises a plurality of ports 11, a plurality of cables 13, a relay 14, a power source 15, and an extraneous personal computing (PC) device 16. The plurality of ports 11 is terminally positioned on the base 10, and the plurality of cables 13 is terminally positioned on the base 10 opposite the plurality of ports 11. The at least one illumination arm 20 comprises a jack 21, an arm 23, a microphone 25, an illumination head 26, a camera 32, a speaker 33, and a plurality of wires 34. The illumination head 26 is terminally positioned on the arm 23 while the jack 21 is terminally positioned on the arm 23 opposite the illumination head 26. Additionally, the jack 21 is mounted to a corresponding one of the plurality of ports 11 of the base 10. The at least one illumination arm 20 is detachably attached to the base 10 through the jack 21, and the illumination head 26 of the at least one illumination arm 20 is connected to the power source 15 through the plurality of cables 13 of the base 10. The at least one actuator 80 is interiorly mounted on the at least one illumination arm 20. Further, the at least one actuator 80 comprises at least one motor 83, which is attached to the at least one actuator 80. Additionally, the at least one motor 83 is configured to drive the at least one actuator 80 to perform linear and rotational movements of the at least one illumination arm 20. The control system 70 is mounted on the base and electrically connected to the power source 15. The control system 70 comprises a processor 71, a plurality of position sensors 72, and an analog/digital (A/D) converter 73. The processor 71 is positioned on the control system 70. The plurality of position sensors 72 is terminally mounted on the at least one illumination arm 20. The A/D converter 73 is positioned on the control system 70. Both the plurality of position sensors 72 and the A/D converter 73 are electrically connected to the processor 71 of the control system 70. Further, the relay 14 of the base 10 is electrically connected with the A/D converter 73 of the control system 70. The at least one motor 83 of the at least one actuator 80 is electrically connected with the relay 14 of the base 10. And the processor 71 of the control system 70 is configured to control the at least one illumination arm 20 to adjust the position and orientation of the illumination head 26 of the at least one illumination arm 20 via inputs of the plurality of position sensors 72 of the control system 70.

As can be seen in FIG. 1 to FIG. 6, in the preferred embodiment of the present invention, the base 10 is cylindrical in shape and accommodating the at least one illumination arm 20 thereon. The base 10 is attached to a ceiling, a wall, or a fixture, by extraneous fasteners or coupling elements that permit the flexible lighting system to be anchored to a particular location overhead of the environment of the medical, dental, or veterinary facility. Although the base 10 is preferably cylindrical, the base 10 may be alternative geometries including, but not limited to, cubic rectilinear, trilinear, domed, arcuate, polygonal, and so on. Additionally, the base 10 may be configured to be installed on an existing light fixture base for retrofitting and/or remodeling purposes. This feature allows a user to efficiently change out an existing lighting system to the present invention. Further, the base 10 comprises an extraneous personal computing (PC) device 16. The PC device 16 may be wirelessly connected to the processor 71 of the control system 70 via a communication network, including, but not limited to, Internet, etc.

As can be seen in FIG. 1 to FIG. 6, and FIG. 10, the plurality of ports 11 is positioned on at least one planar or arcuate surface of the base 10. The individual ports of the plurality of ports 11 accommodate the individual illumination arm 20 through the jack 21 thereof. Each port of the plurality of ports 11 is in connection with the processor 71 of the control system 70 through the plurality of cables 13 spanning through the base 10. Further, the plurality of ports 11 comprises at least three individual ports that are further preferably arranged radially equidistant in the exemplified embodiment. However, a lower or higher count of individual ports of the plurality of ports 11 is feasible to accommodate any number of arms 23 of the at least one illumination arm 20.

As can be seen in FIG. 1 to FIG. 6, and FIG. 10, the microphone 25 is attached to the arm 23 of the at least one illumination arm 20, arbitrarily between the jack 21 and the illumination head 26. Additionally, the microphone 25 is connected to the processor 71 of the control system 70 and the power source 15 of the base 10. The microphone 25 can be used by a user to intercept voice commands of the user and record audio data, comments, narratives through the relay 14 and the processor 71 of the control system 70 during the use of the present invention. As can be seen in FIG. 1 to FIG. 4, the arm 23 of the at least one illumination arm 20 comprises a handle 24, which is exteriorly attached to the arm 23 adjacent the illumination head 26 in the preferred embodiment or arbitrarily along the arm 23 between the microphone 25 and the illumination head 26 in alternative embodiments. The handle 24 allows the user to clasp the handle 24 to direct the illumination head 26 to any arbitrary orientation.

As can be seen in FIG. 1 to FIG. 6, located at one distal end of the individual illumination arm 20 is the jack 21, wherein the jack 21 engages with the individual port of the plurality of ports 11 on the base 10. The jack 21 couples the at least one illumination arm 20 with the base 10, facilitating the transmission of power and information therebetween. The jack 21 preferably is plugged into the individual port of the plurality of ports 11, although other electrical coupling means may be employed such as, but not limited to, USB jacks, power couplers, prongs, and so on. Additionally, the jack 21 of the at least one illumination arm 20 comprises a jack base 22 which is interstitially located between the arm 23 and the jack 21. The jack base 22 comprises a tab or similar to facilitate removal of the at least one illumination arm 20 from the base 21. The jack base 22 may further employ a self-locating geometry that locks the jack 21 into the individual port of the plurality of ports 11 through rotation therein. Through reversing rotation, the at least one illumination arm 20 may be removed. Further, the arm 21 is disposed between the jack base 22 and the illumination head 26 is the arm 23. Wherein the arm 23 preferably comprises a malleable stem that facilitates direction of the illumination head 26 in a particular direction and orientation. The arm 23 further comprises a cavity along the length thereof with the plurality of wires 34 therethrough that connects the jack 21 with the microphone 25, the camera 32, and the speaker 33. The arm 23 may comprise an arbitrary length that may suit the situation and the at least one illumination arm 20 may be removed modularly from the base 10 and replaced with a longer or shorter individual arm 23.

Figure 6:
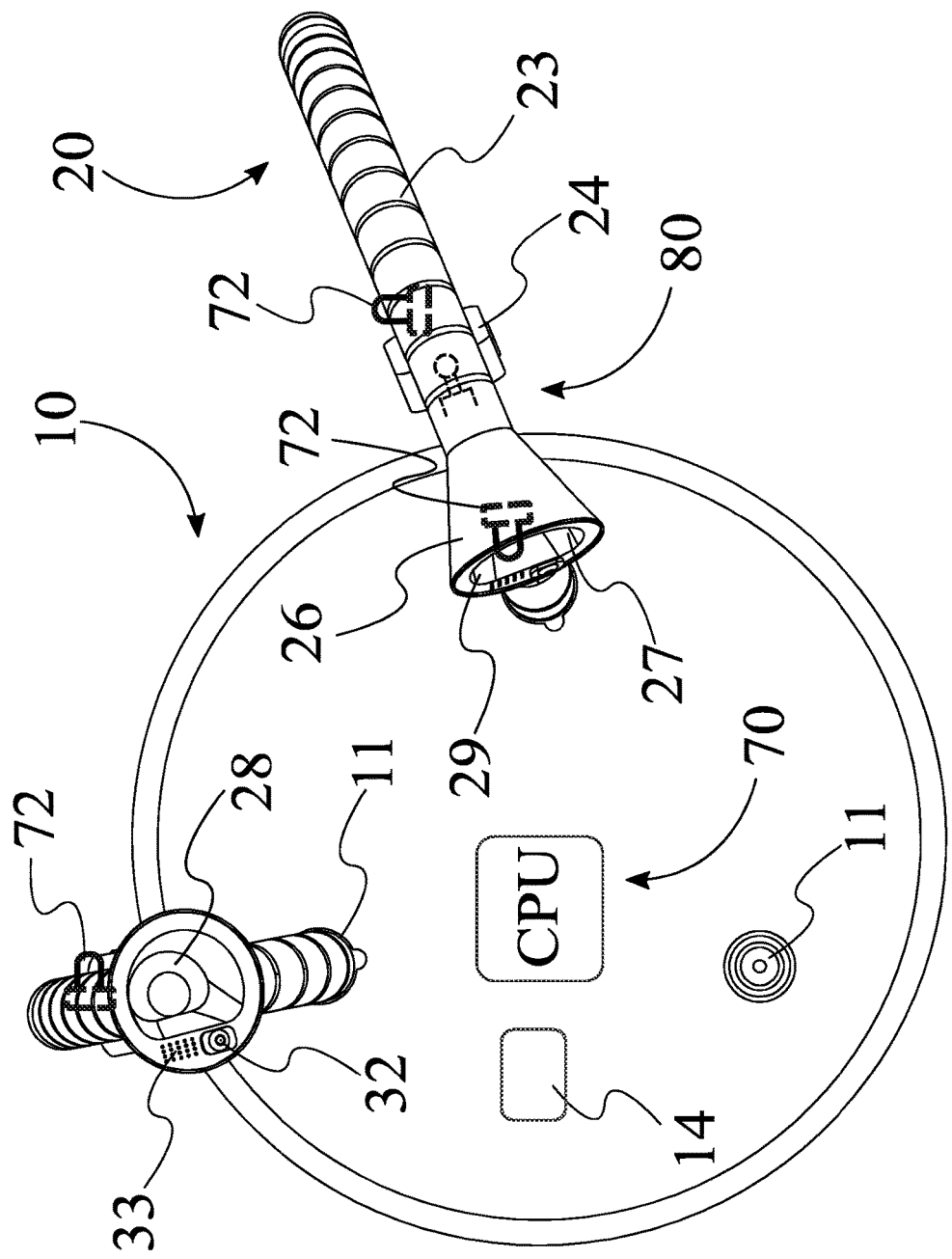
FIG. 6 is a bottom view of the present invention, wherein a speaker is observed adjacent to a camera. Further observed is an optional tab of the base jack on an individual illumination arm and a third port is observed unoccupied.

As can be seen in FIG. 6, the illumination head 26 of the at least one illumination arm 20 comprises an illumination recess 27, an illumination means 28, an illumination cover 29, and a plurality of illumination apertures 31. The camera 32 and speaker 33 of the at least one illumination arm 20 are exteriorly on the illumination head 26. Disposed at the second distal end of the arm 23 opposite the jack 21 and jack base 23 is the illumination head 26. The illumination means 28 is enclosed within the illumination recess 27 of the illumination head 26. The illumination head 26 further comprises the plurality of wires 34 spanning therethrough that connect the illumination means 28, the speaker 33, and the camera 32 with the jack 21. The illumination head 26 may further optionally facilitate swiveling about the distal end of the arm 23. Located at the distal end of the illumination head 26 opposite the arm 23 is the illumination recess 27, whereupon the illumination means 28 is housed therein and opens outward opposite from the arm 23. The illumination recess 27 may accommodate therein optional reflective coating or mirrors about the lateral walls to intensify the light in a particular direction or magnitude. Housed within the illumination recess 27 and disposed on the inner-most planar surface is the illumination means 28. The illumination means 28 facilitates illumination therefrom such as by a bulb, LED, filament, or similar that is connected to the jack 21 through the plurality of wires 34. Located on the distal end of the illumination head 26 opposite the arm 23 is the illumination cover 29, wherein the illumination cover 29 is preferably transparent and may optionally be removable from the illumination head 26 to replace the illumination means 28 within the illumination recess 27. The illumination cover 29 may further possess a plurality of apertures 31 that facilitates transmission of sound and images between the environment, the camera 32, and the speaker 33. Disposed on the distal surface of the illumination head 26 opposite the arm 23 is the camera 32. Wherein the camera 32 is accommodated by the planar surface of the illumination head 26 shared by the speaker 33 and the illumination recess 27. The camera 32 is in connection to the jack 21 through the plurality of wires 34 spanning through the arm 23. The camera 32 may be engaged autonomously, remotely, or by voice command and thereafter capturing video or images in the orientation that the illumination head 26 is directed to. Further disposed on the distal planar surface of the illumination head 26 shared with the camera 32 is the speaker 33. The speaker 33 is exteriorly positioned on the illumination head 26 and in connection to the jack 21 through the plurality of wires 34 spanning through the arm 23. The speaker 33 may output sound, music, and engage in communication between an extraneous PC device 16 of the base 10, when the at least one illumination arm 20 is engaged with the base 10, connecting the jack 21 to the processor 12.

Figure 8:
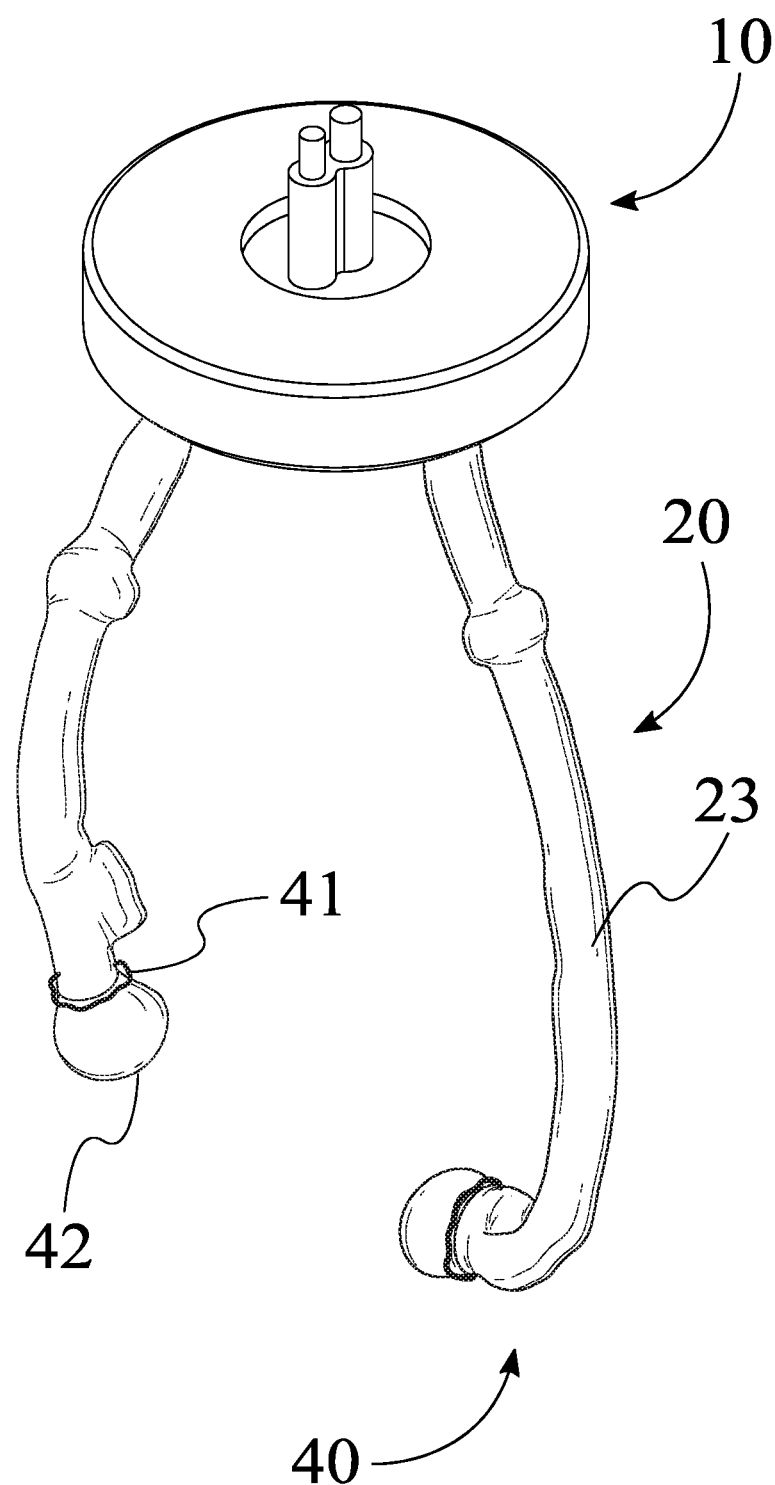
FIG. 8 is perspective view of an alternative embodiment of the present invention, wherein illumination arms of the smart flexible lighting system are sealed with covers.
Figure 9:
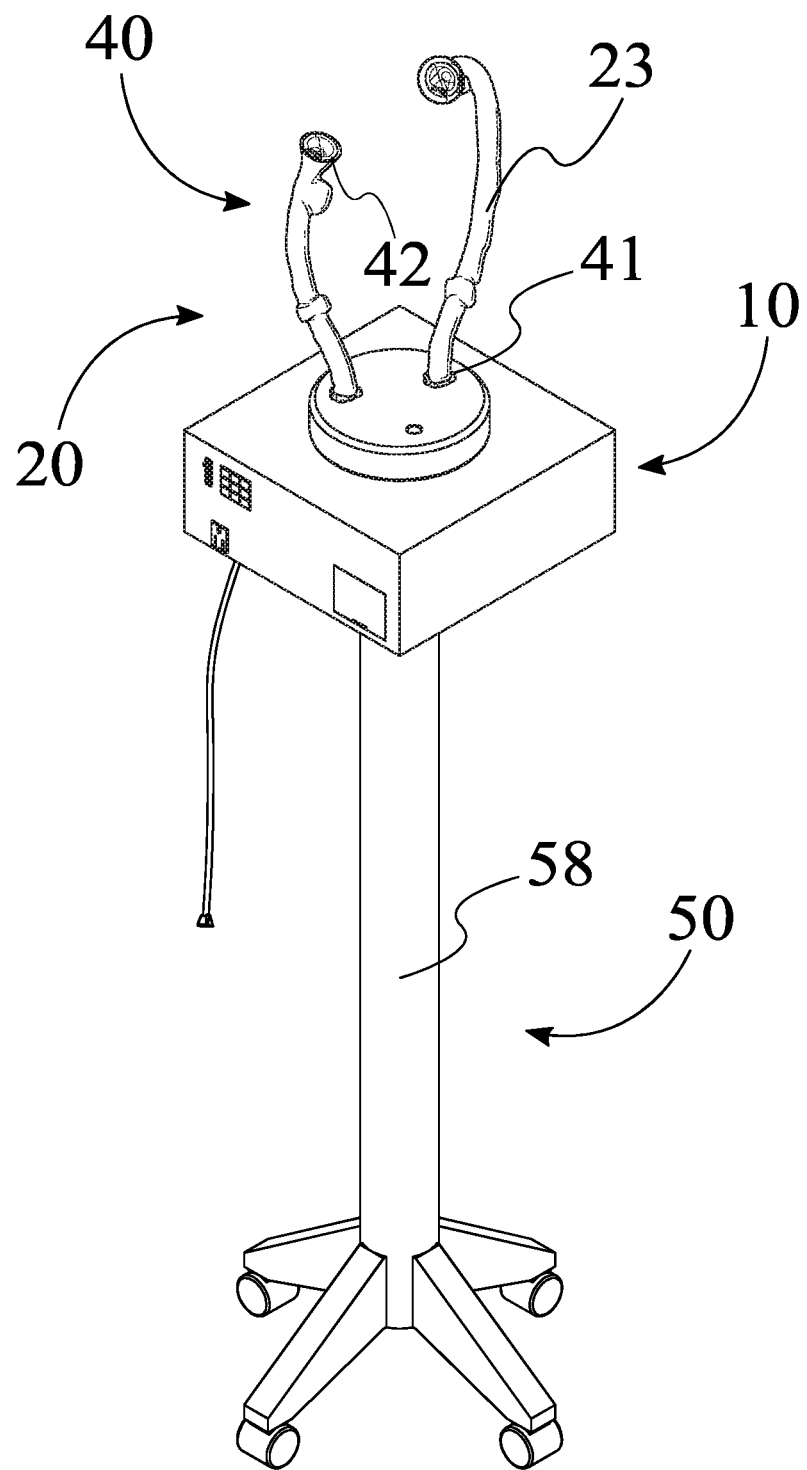
FIG. 9 is perspective view of another embodiment of the present invention, wherein illumination arms of the mobile embodiment of the smart flexible lighting system are sealed with covers.

As can be seen in FIG. 8 to FIG. 9, the smart flexible lighting system of the present invention further comprises a cover 40, which comprises a cover fastener 41 and a front end 42. The cover 40 may be attached over the individual arm of the at least one illumination arm 20. In the preferred embodiment of the present invention, the front end 42 of the cover 40 is positioned on the cover 40 adjacent the illumination head 26 of the at least one illumination arm 20 and may be a transparent or translucent end that facilitates transmission of illumination and vision therethrough. Additionally, the cover may be disposable and is generally tubular in shape. Located preferably along the rim of the cover 40 is the cover fastener 41 that facilitates the attachment of the cover 40 to the arm 23 of the at least one illumination arm 20. More specifically, the cover fastener 41 is exteriorly positioned on the cover 40 to seal the at least one illumination arm 20 within the cover 40. Thus, the cover fastener 41 mitigates the removal of the cover 40 until engaged by the user to remove. Preferably, the cover fastener 41 comprises a clamp or clipping means that couples to the arm 23, although other cover fastening means may be employed including, but not limited to, elastic apertures and bands, snap fits, and so on. Further, the cover fastener 41 may necessitate a complementing cover fastening means on the arm 23.

As can be seen in FIG. 1 to FIG. 6, and FIG. 10, the at least one actuator 80 comprises a first actuator 81, a second actuator 82, and the at least one motor 83. The at least one motor 83 is mounted on each of the first actuator 81 and the second actuator 82. Specifically, the first actuator 81 may include, but is not limited to, a translational actuator. The first actuator 81 is configured to provide linear motions to the illumination head 26 of the at least one illumination arm 20. Further, the second actuator 82 may include, but is not limited to, a rotational actuator. The second actuator 82 is configured to provide rotational motions to the illumination head 26 of the at least one illumination arm 20. With the first actuator 81 and the second actuator 82 of the at least one actuator 80, the at least one illuminator arm 20 of the present invention can move to any desired geographical position, direction, and/or orientation in any of the medical, dental, or veterinary facilities. The motor 83 is necessary to exert a force needed to propel the at least one illumination arm 20 in the desired direction. In order to control the movement of the at least one illumination arm 20, the control system 70 is necessary. The control system 70 takes inputs from the user via the microphone 25 of the at least one illumination arm 20, and/or the extraneous PC device 16. Then the control system 70 processes the inputs via the processor 71. Subsequently, for a desired movement, the control system 70 generates an output in the form of a system response and sends it to the at least one actuator 80 to perform the desired movements of the at least one illumination arm 20. The control system 70 also acquires inputs from the plurality of position sensors 72 in numerous places along the at least one illumination arm 20 which are electrically connected to the control system 70 via cables/wires, and/or wirelessly, spanning the at least one illumination arm 20 for each of the plurality of position sensors 72. The plurality of position sensors 72 provides feedback to the control system 70 to allow for precise tuning of the location and orientation of at least one illumination arm 20 in reference to the desired position and orientation. The output of the control system 70 is where the at least one illumination arm 20 is after being moved and the control system 70 loops using the feedback from the plurality of position sensors 72 at each move until the at least one illumination arm 20 has finally been positioned properly according to the desired location and orientation inputs. The movement directions can include, but are not limited to, longitudinal, lateral, vertical, and rotational movement, etc.

As can be seen in FIG. 1 to FIG. 6, the control system 70 is housed arbitrarily within the base 10 and in connection to the plurality of cables 13. Specifically, the control system 70 executes the functions and interprets the data from the microphone 25, the camera 32, and the extraneous PC device 16 of the base 10. Additionally, the relay 14 permits the lighting system to facilitate wireless communications with an extraneous PC device 16 or any other device such as a display. The relay 14 is attached to the base 10 adjacent to the control system 70. Spanning through the body in connection between the control system 70 and the jack 21 of the at least one illumination arm 20, and further between the control system 70 and an extraneous power grid of the particular facility is the plurality of cables 13. The plurality of cables 13 facilitates the transmission of power and information therethrough. Additionally, the plurality of cables 13 may further comprise a disparate number of diameters therebetween where thinner cables are employed within the base 10 and thicker cables are employed between the base 10 and the extraneous ceiling, wall, or fixture. The power source 15 is electrically connected to both the control system 70 and the relay 14. The at least one illumination arm 20 is coupled with the base 10 through the jack 21 and an individual port of the plurality of ports 11, wherein the at least one illumination arm 20 may comprise a count up to the count of the plurality of ports 11. Additionally, the at least one illumination arm 20 comprises a plurality of wires 34 that span along the at least one illumination arm 20 to the illumination head 26.

As can be seen in FIG. 5 to FIG. 6, and FIG. 10 to FIG. 11, the control system 70 of the present invention comprises the processor 71, the analog/digital (A/D) converter 73, a graphical processing unit (GPU) 74, and a cooling system 75. Specifically, the GPU 74 is mounted to the control system 70 and the cooling system 75 is amounted to the control system 70 adjacent to the GPU 74. Additionally, the cooling system 75 is electrically connected to the GUP 74 and the GPU 74 is electrically connected to the processor 71 of the control system 70. In the preferred embodiment of the present invention, the GPU 74 may be directly connected to the housing chip of the processor 71, for example, a motherboard on a personal computing (PC) device 16 and facilitates direct linking to the processor 71. Since a GPU 74 enables image processing many times faster than that of a processor 71 thus the GPU 74 may be a necessity if the arm 23 of the at least one illumination arm 20 is to move at any reasonable speed. The benefits of the GPU 74 lie in the ability to perform extremely fast and parallelized operations, multiple at once, which would be a necessity if continuous image data is to be processed efficiently. In general, GPUs tend to generate a lot of heat so the cooling system 75 may be essential given that the processor 71 is already near the GPU 74. The cooling system 75 may include, but is not limited to, multiple fans or more complex yet effective option of liquid cooling. With the GPU 74, the present invention is able to directly process video inputs from the camera 32 of the at least one illumination arm 20 and autonomously move the at least one illumination arm 20.

Figure 10:
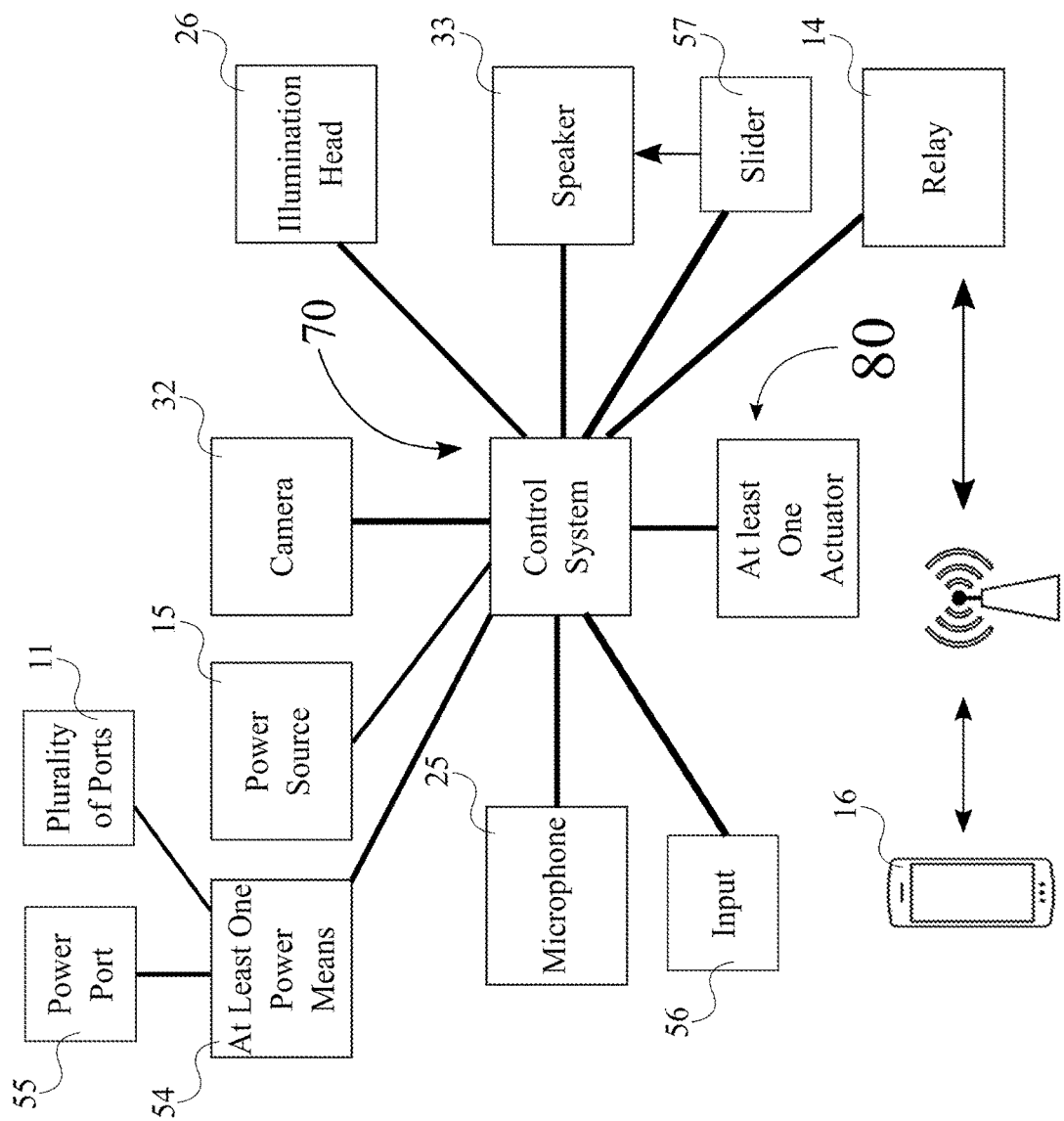
FIG. 10 is an electrical diagram of the smart flexible lighting system of the present invention.
Figure 11:
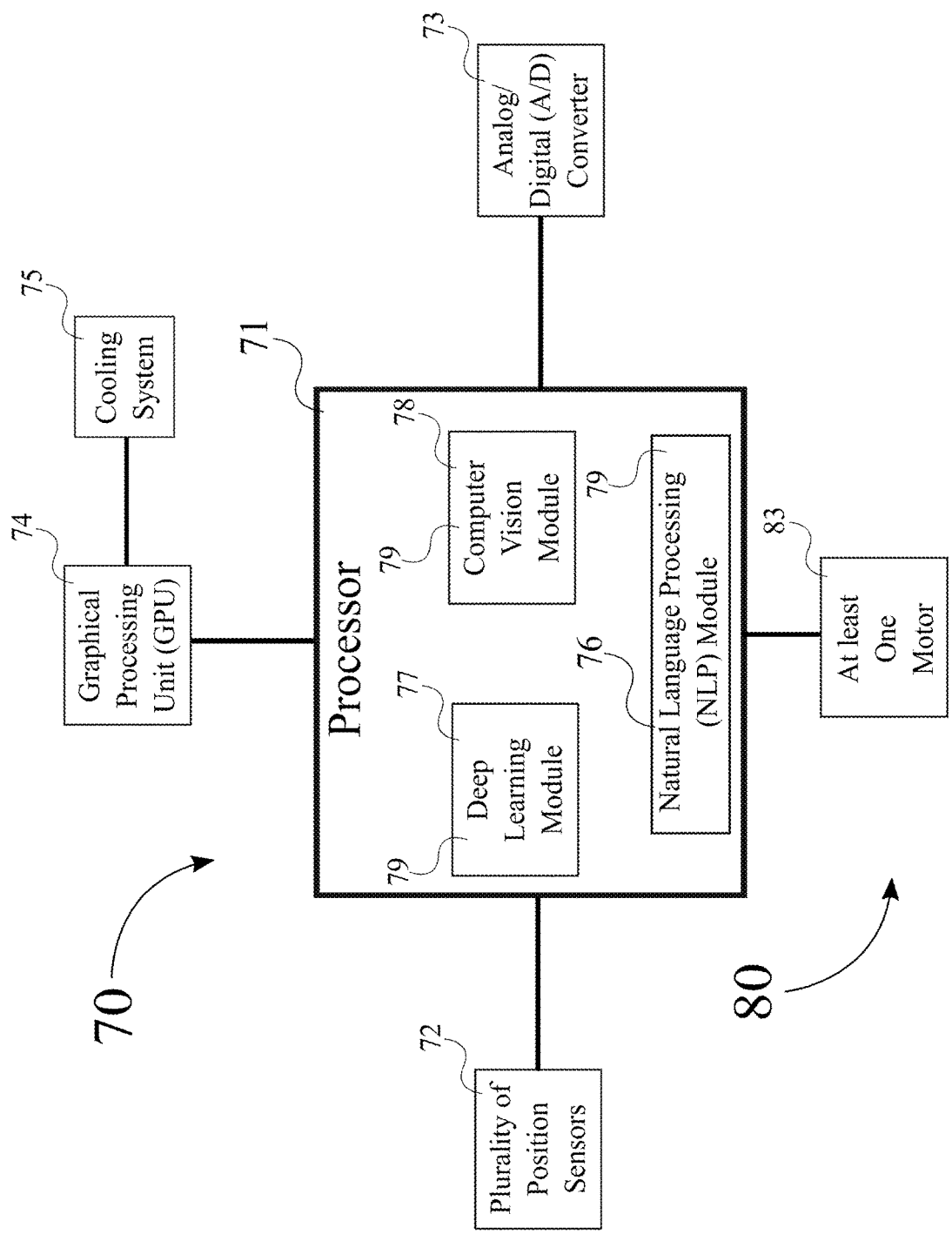
FIG. 11 is an electrical diagram of the control system with multiple inputs of the smart flexible lighting system of the present invention.

As can be seen in FIG. 10 to FIG. 11, the processor 71 of the control system 70 of the present invention comprises at least one artificial intelligence (AI) module 79. In the preferred embodiment, the AI module 79 is used to substantially enhance the capabilities of the present invention. The AI module 79 allows for the user to direct the at least one illumination arm 20 by voice commands received from the microphone 25 of the at least one illumination arm 20 and/or the extraneous PC device 16, or to facilitate at least one illumination arm 20 move autonomously by recognizing visual inputs from the camera 32 of at least one illumination arm 20. Specifically, the AI module 79 is configured to process inputs from at least one of the plurality of position sensors 72 of the control system 70, microphone 25 of the at least one illumination arm 20, and the camera 32 of the at least one illumination arm 20. Additionally, the processor 71 is configured to move the illumination head 26 of the at least one illumination arm 20 to a specific geographic position and a specific orientation via the at least one AI module 79. More specifically, the AI module 79 comprises a natural language processing (NLP) module 76, a deep learning module 77, and a computer vision module 78.

As can be seen in FIG. 10 to FIG. 11, The processor 71 of the control system 70 is configured to facilitate communications between the control system 70 and the user PC device 16 of the base 10 via the NLP module 76. Additionally, the processor 71 of the control system 70 may configured to facilitate communications between the control system 70 and a user via the NLP module 76 of at least one AI module 79, the speaker 33 and the microphone 25 of the at least one illumination arm 20. In order to process the voice inputs from the microphone 25 of the at least one illumination arm 20, made by the user, the processor 71 runs the NLP module 76 to convert human speech into something the processor 71 can interpret. After the input is received from the microphone 25 of the at least one illumination arm 20 in the form of an analog signal, the analog signal is converted to a digital signal used by the processor 71 via the A/D converter 73, which is connected between the microphone 25 of the at least one illumination arm 20 and processor 71 through cables/wires or wirelessly. Since the signal feeds an input sentence (string) to the processor 71, the signal needs to be further converted into binary data (1's and 0's) by the A/D converter 73 and have the meanings of each word embedded in a dictionary housed in the processor 71. The converted signal is then used by the NLP module 76, wherein the NLP module 76 processes the input signal and executes an appropriate response/output for the specified input. For example, if the user tells the at least one illumination arm 20 to rotate 90 degrees to change the direction/orientation of the illumination head 26, the input is processed and then sent to the control system 70 as the input to the processor 71 of the control system 70. Subsequently, the processor 71 sends out an output to the at least one actuator 80 to perform the desired movements via the at least one motor 83 of the at least one actuator 80 and the plurality of positional sensors 72 of the control system 70 until the at least one illumination arm 20 has reached the specified location and/or direction/orientation.

Further, to enable autonomous movements of the at least one illumination arm 20, all image data received from the camera 32 of the at least one illumination arm 20 in real time is fed to the computer vision module 78. The computer vision module 78 subsequently takes the input and feeds into the deep learning module 77, wherein the deep learning module 77 gets trained to interpret the images and to make appropriate decisions to actuate the at least one actuator 80 to perform required motions accordingly. As an example, if the deep learning module 77 sees that the light in the area the surgeon is operating is not adequate, after training, the deep learning module 77 can send an input to the control system 70 to reposition the at least one illumination arm 20 according to where the light is needed.

Figure 7:
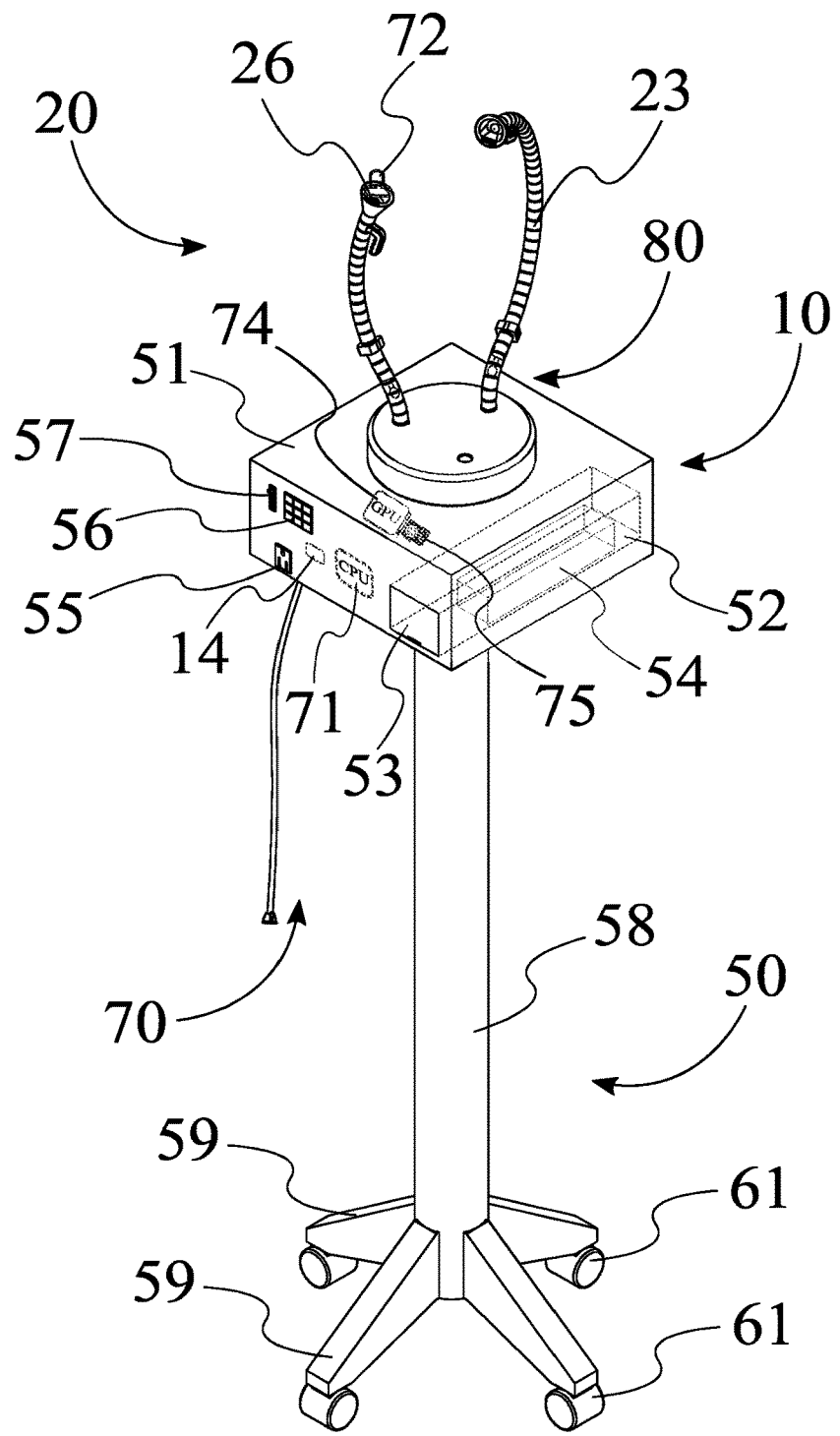
FIG. 7 is a perspective view of the mobile embodiment of the present invention, wherein a stand with a plurality of wheels supporting the smart flexible lighting system of the present invention is observed with a stand casing being underneath the base that is now vertically reversed.

As can be seen in FIG. 7, the smart flexible lighting system of the present invention comprises a stand 50. The stand 50 comprises a stand casing 51, a column 58, a plurality of legs 59, and a plurality of wheels 61. The stand casing 51 is distally and terminally attached to the column 58. The plurality of legs 59 is distally and terminally attached to the column 58 opposite the stand casing 51. Additionally, the plurality of legs 59 is perimetrically distributed on the column 58 and each of the plurality of wheels 61 is terminally attached to one of the plurality of legs 59. Further, the base 10 is exteriorly mounted to the stand casing 51 opposite the column 58 of the stand 50. Located atop the column 58 of the stand 50 is the stand casing 51. The stand casing 51 comprises the stand casing comprises a power storage enclosure 52, at least one power means 54, at least one power port 55, at least one input 56, and at least one slider 57. The power storage enclosure 52 is positioned inside the stand casing 51 and comprises a detachable enclosure door 53. The detachable enclosure door 53 is mounted on and flush with the exterior surface of the base 10. The at least one power means 54 is detachably mounted to the interior of the power storage enclosure 52. The at least one power port 55 is mounted to and flush to the exterior surface of the stand casing 51. Both the at least one input 56 and the at least one slider 57 are mounted to the exterior surface of the stand casing 51 adjacent the at least one power port 55. The at least power port 55 is electrically connected to the at least one power means 54. The at least one input 56 is electrically connected to the at least one power means 54. The at least one slider 57 is electrically connected to the at least one power means 54, and the at least one slider 57 is electrically connected to the illumination head 26 of the at least one illumination arm 20, as can be seen in FIG. 8.

Preferably the stand casing 51 comprises a cubic rectilinear profile with planar lateral walls and a planar top surface that the base 10 rests upon. The stand casing 51 is further preferably hollow, accommodating the power storage enclosure 52, the at least one power means 54, the at least one power port 55, the at least one input 56, and the at least one slider 57 on the exterior and the interior of the stand casing 51. Preferably located along one of the lateral walls of the stand casing 51 at an arbitrary height thereof is the power storage enclosure 52. The power storage enclosure 52 is recessed within the stand casing 51 and houses the at least one power means 54 therein. The power storage enclosure 2 is preferably rectilinear in profile and associated to the lateral wall of the stand casing 51 by a hinge on the enclosure door 53, thus allowing the power storage enclosure 52 to be opened and closed, exposing the at least one power means 54 therein. However other power enclosures may be employed including, but not limited to, sliding panels, snap fitting panels, and so on. The stand casing 51 may further comprise the processor 12, the relay 14, and the PC device 16. The relay 14 is exteriorly attached to the stand casing 51. The processor 12 attached to stand casing 51 adjacent the relay 14. The processor 12 is electrically connected to the relay 14, the at least one input 56, the at least one power means 54, and both the speaker 32 and the camera 33 of the at least one illumination arm 20. Further, the processor 12 is connected to the PC device 16 through the relay 14 over an external communication network.

As can be seen in FIG. 7, the at least one power means 54 is preferably housed within the power storage enclosure 52. The at least one power means 54 may comprise either a battery, a wall outlet cable, or multiple power means. The processor 12 of the base 10 may regulate the use of energy from the at least one power means 54. Further, the at least one power means 54 may facilitate recharging where two or more power means are employed by the present invention, whereupon the processor 12 regulates the distribution of electrical power. Disposed preferably upon one of the lateral walls of the stand casing 51 shared by the power storage enclosure 52 is the at least one power port 55. The at least one power port 55 preferably comprises an outlet that an AC (alternating current) cord may plug into, drawing power for an extraneous device from the at least one power means 54.

Further preferably disposed along one of the lateral walls of the stand casing 51, shared by the power storage enclosure 52 and the at least one power port 55 is the at least one input 56, which may be electrically connected with components including, but not limited to, the microphone 25, the camera 33, etc., of the at least one illumination arm 20. The user may engage to control the functionality of the at least one illumination arm 20 regarding light control, intensity, and activation of the speaker 33, microphone 25, and/or camera 32. Preferably the at least one input 56 comprises a depressible key or a plurality thereof in a keypad configuration. The at least one input 56 may further be embodied by a touchscreen controller to facilitate similar commands. Further disposed along a lateral wall coincident with and adjacent to the at least one input 56 is the at least one slider 57. The at least one slider 57 may facilitate a switching state consequent to the tiers of the slider, or an analog slider to vary the intensity of the illumination means 28 of the at least one illumination arm 20 and the speaker 33. Protruding beneath the stand casing 51 and above the plurality of legs 59 is the column 58. The column 58 raises the stand casing 51 an arbitrary height above the ground. Additionally, the column 58 may comprise a telescoping column or pin lock to adjust the height of the column 58. Located near the bottom of the column 58 and preferably protruding from the longitudinal surfaces of the column 58 is the plurality of legs 59. The plurality of legs 59 preferably protrudes outward from the center of the column 58 and rest atop a plurality of wheels 61. Connected to the plurality of legs 58 and preferably in a count equivalent thereto is the plurality of wheels 61. The plurality of wheels 61 facilitates mobility of the stand 50. Optionally, the plurality of wheels 61 may individually comprise wheel locks that arrest rotation, thus arresting the motion of the stand 50.

Although the invention has been explained in relation to its preferred embodiment, it is to be understood that many other possible modifications and variations can be made without departing from the spirit and scope of the invention as hereinafter claimed.

What is claimed is:

1. A smart flexible lighting system for medical, dental, and veterinary facilities comprising:
   a base;
   at least one illumination arm;
   at least one actuator;
   a control system;
   the base comprising a plurality of ports, a plurality of cables, a power source, and a relay;
   the plurality of ports being terminally positioned on the base;
   the relay being positioned on the base adjacent to the plurality of ports;
   the plurality of cables being terminally positioned on the base opposite the plurality of ports;
   the at least one illumination arm comprising a jack, an arm, and an illumination head;
   the illumination head being terminally positioned on the arm;
   the jack being terminally positioned on the arm opposite the illumination head;
   the jack being mounted to one of the plurality of ports of the base;
   the at least one illumination arm being detachably attached to the base through the jack;
   the illumination head of the at least one illumination arm being connected to the power source through the plurality of cables of the base;
   the at least one actuator being interiorly mounted on the at least one illumination arm;
   the at least one actuator comprising at least one motor;
   the at least one motor being attached to the at least one actuator;
   wherein the at least one motor is configured to drive the at least one actuator to perform linear and rotational movements of the at least one illumination arm;
   the control system being mounted on the base;
   the control system being electrically connected to the power source;
   the control system comprising a processor, a plurality of position sensors, and an analog/digital (A/D) converter;
   the processor being positioned on the control system;
   the plurality of position sensors being terminally mounted on the at least one illumination arm;
   the A/D converter being positioned on the control system;
   both the plurality of position sensors and the A/D converter being electrically connected to the processor of the control system;
   the relay of the base being electrically connected with the A/D converter of the control system;
   the at least one motor of the at least one actuator being electrically connected with the relay of the base; and
   wherein the processor of the control system is configured to control the at least one illumination arm to adjust the position and orientation of the illumination head of the at least one illumination arm via inputs of the plurality of position sensors of the control system.

2. The smart flexible lighting system for flexible lighting system for medical, dental, and veterinary facilities as claimed in claim 1 comprising:
the at least one illumination arm comprising a microphone, a camera and a speaker;
the microphone being attached to the at least one illumination arm between the illumination head and the jack;
the microphone being electrically connected with the processor of the control system;
both the camera and the speaker being exteriorly positioned on the illumination head; and
both the camera and the speaker being electrically connected with the processor of the control system.

3. The smart flexible lighting system for flexible lighting system for medical, dental, and veterinary facilities as claimed in claim 2, wherein:
the control system comprises a graphical processing unit (GPU) and a cooling system;
wherein the GPU is mounted to the control system;
wherein the cooling system is mounted to the control system adjacent to the GPU;
wherein the cooling system is electrically connected to the GUP; and
wherein the GPU is electrically connected to the processor of the control system.

4. The smart flexible lighting system for flexible lighting system for medical, dental, and veterinary facilities as claimed in claim 3, wherein:
the processor of the control system comprises at least one artificial intelligence (AI) module;
wherein the AI module is configured to process inputs from at least one of the plurality of position sensors of the control system, microphone of the at least one illumination arm, and the camera of the at least one illumination arm;
wherein the processor is configured to move the illumination head of the at least one illumination arm to a specific geographic position and a specific orientation via the at least one AI module.

5. The smart flexible lighting system for flexible lighting system for medical, dental, and veterinary facilities as claimed in claim 4, wherein the at least one AI module comprises a computer vision module.

6. The smart flexible lighting system for flexible lighting system for medical, dental, and veterinary facilities as claimed in claim 4, wherein the at least one AI module comprises a deep learning module.

7. The smart flexible lighting system for flexible lighting system for medical, dental, and veterinary facilities as claimed in claim 4, wherein:
the at least one AI module comprises a natural language processing (NLP) module; and
wherein the processor of the control system is configured to facilitate communications between the control system and a user personal computing (PC) device via the NLP module.

8. The smart flexible lighting system for flexible lighting system for medical, dental, and veterinary facilities as claimed in claim 7, wherein the processor of the control system is configured to facilitate communications between the control system and a user via the NLP module of at least one AI module, the speaker and the microphone of the at least one illumination arm.

9. The smart flexible lighting system for medical, dental, and veterinary facilities in claim 1 comprising:
the at least one illumination arm comprising a handle;
the handle being exteriorly attached to the at least one illumination arm; and
the handle being positioned on the at least one illumination arm adjacent to the illumination head.

10. The smart flexible lighting system for medical, dental, and veterinary facilities in claim 1 comprising:
the at least one actuator comprising a first actuator;
the at least one motor of the at least one actuator being mounted to the first actuator;
the first actuator being a translational actuator; and
wherein the first actuator is configured to provide linear motions to the illumination head of the at least one illumination arm.

11. The smart flexible lighting system for medical, dental, and veterinary facilities in claim 1 comprising:
the at least one actuator comprising a second actuator;
the at least one motor of the at least one actuator being mounted to the second actuator;
the second actuator being a rotational actuator; and
wherein the second actuator is configured to provide rotational motions to the illumination head of the at least one illumination arm.

12. The smart flexible lighting system for medical, dental, and veterinary facilities in claim 1 comprising:
the base comprising an extraneous personal computing (PC) device; and
the PC device being wirelessly connected to the processor of the control system via a communication network.

13. The smart flexible lighting system for medical, dental, and veterinary facilities in claim 1 comprising:
a cover;
the cover comprising a cover fastener;
the cover being exteriorly attached to the at least one illumination arm;
the cover fastener being exteriorly and distally positioned on the cover; and
wherein the cover fastener seals the at least one illumination arm inside the cover.

14. The smart flexible lighting system for medical, dental, and veterinary facilities in claim 13 comprising:
the cover comprising a front end;
the front end being positioned on the cover adjacent to the illumination head of the at least one illumination arm; and
wherein the front end is transparent or translucent to allow light of the illumination head going through.

15. The smart flexible lighting system for medical, dental, and veterinary facilities in claim 1, wherein the base is configured to be installed on the existing light fixture bases.

16. The smart flexible lighting system for medical, dental, and veterinary facilities claimed in claim 1 comprising:
a stand;
the stand comprising a stand casing, a column, a plurality of legs, and a plurality of wheels;
the stand casing being distally and terminally attached to the column;
the plurality of legs being distally and terminally attached to the column opposite the stand casing;
the plurality of legs being perimetrically distributed on the column;
each of the plurality of wheels being terminally attached to one of the plurality of legs; and
the base being exteriorly mounted to the stand casing opposite the column.

17. The flexible lighting system for medical, dental, and veterinary facilities as claimed in claim 16 comprising:

the stand casing comprising a power storage enclosure, at least one power means, at least one power port, at least one input, at least one slider;

the power storage enclosure being positioned inside the stand casing;

the power storage enclosure comprising a detachable enclosure door;

the detachable enclosure door being mounted on and flush with the exterior surface of the base;

the at least one power means being detachably mounted to the interior of the power storage enclosure;

the at least one power port being mounted to and flush to the exterior surface of the stand casing;

both the at least one input and the at least one slider being mounted to the exterior surface of the stand casing adjacent the at least one power port;

the at least power port being electrically connected to the at least one power means;

the at least one input being electrically connected to the at least one power means;

the at least one slider being electrically connected to the at least one power means; and the at least one slider being electrically connected to the illumination head of the at least one illumination arm.

18. The flexible lighting system for medical, dental, and veterinary facilities as claimed in claim 17, wherein the at least one input is electrically connected with the microphone of the at least one illumination arm.

19. The flexible lighting system for medical, dental, and veterinary facilities as claimed in claim 17, wherein the at least one input comprising a touchscreen controller.

20. The flexible lighting system for medical, dental, and veterinary facilities as claimed in claim 17 comprising:

the stand casing comprising a processor, a relay, and a PC device;

the relay being exteriorly attached to the stand casing;

the processor being attached to stand casing adjacent the relay;

the processor being electrically connected to the relay;

the processor being electrically connected to the at least one input;

the processor being electrically connected to the at least one power means;

both the speaker and the camera of the at least one illumination arm being electrically connected to the processor; and the processor being connected to the PC device through the relay over an external communication network.

* * * * *